(12) United States Patent
Kraft

(10) Patent No.: US 7,384,906 B2
(45) Date of Patent: Jun. 10, 2008

(54) ALIPHATIC COMPOUNDS AS FRAGRANTS WITH MUSK CHARACTERISTICS

(75) Inventor: Philip Kraft, Dübendorf (CH)

(73) Assignee: Givandan SA, Vernier (CH)

( * ) Notice: Subject to any disclaimer, the term of this patent is extended or adjusted under 35 U.S.C. 154(b) by 578 days.

(21) Appl. No.: 10/535,974

(22) PCT Filed: Nov. 24, 2003

(86) PCT No.: PCT/CH03/00773

§ 371 (c)(1),
(2), (4) Date: May 24, 2005

(87) PCT Pub. No.: WO2004/050595

PCT Pub. Date: Jun. 17, 2004

(65) Prior Publication Data

US 2006/0052277 A1    Mar. 9, 2006

(30) Foreign Application Priority Data

Nov. 29, 2002   (GB) .................................. 0227867.9
Aug. 15, 2003   (GB) .................................. 0319190.5

(51) Int. Cl.
A61Q 13/00   (2006.01)
(52) U.S. Cl. ........................................ 512/25; 558/269
(58) Field of Classification Search ............. 512/25; 558/260
See application file for complete search history.

(56) References Cited

U.S. PATENT DOCUMENTS 5,166,412 A    11/1992   Giersch et al. ............. 560/231
5,936,100 A  *  8/1999   Furstner et al. ............. 549/266

FOREIGN PATENT DOCUMENTS

EP    1262474 A1    12/2002

OTHER PUBLICATIONS

STIC Search Report dated Jan. 30, 2008.*
International Search Report dated Mar. 8, 2004 for application PCT/CH03/00773.
Search Report dated Apr. 17, 2003 from The Patent Office in Great Britain for application GB 0227867.9.
Journal of Chromatography, vol. 39, No. 1, 1969, (Stern Robert L. et al), pp. 17-32.

* cited by examiner

*Primary Examiner*—Eisa B Elhilo
(74) *Attorney, Agent, or Firm*—Norris McLaughlin & Marcus, PA

(57) ABSTRACT

This invention relates to aliphatic carbonyl compounds of formula I wherein, their manufacture and their use in fragrance compositions. R1 to R4, X and Y have the meaning as described in the specification (I)

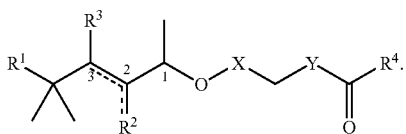

10 Claims, No Drawings

ALIPHATIC COMPOUNDS AS FRAGRANTS WITH MUSK CHARACTERISTICS

FIELD OF THE INVENTION

This invention relates to novel compounds having musk characteristics, their manufacture and their use in fragrance compositions.

BACKGROUND OF THE INVENTION

Conventional compounds having musk characteristics have been selected from nitro arenes, polycyclic aromatics and macrocyclic compounds. However, in recent years there has been great activity to find novel compounds having musk characteristics to replace these conventional musks, the use of which is becoming more restricted because of, e.g. environmental concerns.

Already more than ten years ago the first alicyclic compounds having musk characteristics have been described, exemplified by the product Helvetolide® (4-(3,3-dimethyl-1-cyclohexyl)-2,2-dimethyl-3-oxapentyl propionate, trademark of Firmenich SA, Switzerland).

SUMMARY OF THE INVENTION

Surprisingly, we now found certain aliphatic carbonyl compounds that have musk characteristics and a high impact in perfume formulations. This new class of compounds has not been described before in the literature.

DETAILED OF THE INVENTION

Thus, the present invention refers in a first aspect to a compound of formula I

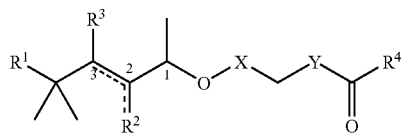

wherein
$R^1$ and $R^3$ are independently hydrogen, methyl, or ethyl;
$R^2$ is hydrogen, methyl, ethyl, methylene, or ethylidene;
$R^4$ is $C_1$ to $C_4$ alkyl, for example methyl, ethyl, i-propyl, n-propyl, cyclopropyl, sec-butyl, n-butyl, tert-butyl, or cyclobutyl; or
$R^4$ is vinyl or a linear, branched or cyclic $C_3$ to $C_4$ alkenyl, for example propen-1-yl, propen-2-yl, prop-2-en-1-yl, cyclobut-1-en-1-yl, butenyl, e.g. but-1-en-1-yl, or butadiene;
X is carbonyl or a divalent radical —(CMe$_2$)-;
Y is oxygen or a divalent radical —(CH$_2$)—;
the bond between C-2 and $R^2$ is a single bond, and the bond between C-2 and C-3 together with the dotted line represents a double bond; or
the bond between C-2 and C-3 is a single bond, and the bond between C-2 and $R^2$ together with the dotted line represents a double bond; or
the bond between C-2 and $R^2$ is a single bond and the bond between C-2 and C-3 is a single bond.

The compounds according to the present invention comprise one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective syntheses.

Preferred compounds are unsaturated aliphatic carbonyl compounds of formula I, i.e. compounds of formula I wherein the bond between C-2 and $R^2$ is a single bond, and the bond between C-2 and C-3 together with the dotted line represents a double bond; or the bond between C-2 and C-3 is a single bond, and the bond between C-2 and $R^2$ together with the dotted line represents a double bond, e.g. acetic acid 2'-methyl-2'-(1",2",4"-trimethylpent-2"-enyloxy)propyl ester, propionic acid 2'-methyl-2'-(1",2",4"-trimethylpent-2"-enyloxy)-propyl ester, cyclopropanecarboxylic acid 2'-methyl-2'-(1",2",4"-trimethylpent-2"-enyloxy)propyl ester, butyric acid 2'-methyl-2'-(1",2",4"-trimethylpent-2"-enyloxy)propyl ester, isobutyric acid 2'-methyl-2'-(1",2",4"-trimethylpent-2"-enyloxy)propyl ester, 2-methylacrylic acid 2'-methyl-2'-(1",2",4"-trimethylpent-2"-enyloxy)propyl ester, but-2-enoic acid 2'-methyl-2'-(1",2",4"-trimethylpent-2"-enyloxy)propyl ester, but-3-enoic acid 2'-methyl-2'-(1",2",4"-trimethylpent-2"-enyloxy)propyl ester, propionic acid (1",2",4"-trimethylpent-2"-enyloxy)carbonylmethyl ester, 6-methyl-6-(1',2',4'-trimethylpent-2'-enyloxy)heptan-3-one, propionic acid 2'-methyl-2'-(1",4",4"-trimethylpent-2"-enyloxy)-propyl ester, cyclopropanecarboxylic acid 2'-methyl-2'-(1",4",4"-trimethylpent-2"-enyloxy)propyl ester, butyric acid 2'-methyl-2'-(1",4",4"-trimethylpent-2"-enyloxy)propyl ester, 4-oxopentanoic acid 1',4',4'-trimethylpent-2'-enyl ester, propionic acid 2'-(1",4"-dimethylpent-2"-enyloxy)-2'-methylpropyl ester and cyclopropanecarboxylic acid 2'-(1",4"-dimethylpent-2"-enyloxy)-2'-methylpropyl ester.

Particular preferred compounds of formula I are represented by the general formula

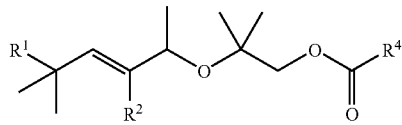

wherein
$R^1$ and $R^2$ are independently hydrogen or methyl;
$R^4$ is $C_1$ to $C_4$ alkyl, for example methyl, ethyl, i-propyl, n-propyl, cyclopropyl, sec-butyl, n-butyl, tert-butyl, or cyclobutyl; or
$R^4$ is vinyl or a linear, branched or cyclic $C_3$ to $C_4$ alkenyl, for example propen-1-yl, propen-2-yl, prop-2-en-1-yl, cycloprop-1-en-1-yl, cycloprop-2-en-1-yl, cyclobut-2-en-1-yl, butenyl, e.g. but-1-en-1-yl, or butadiene.

Compounds of formula I wherein the bond between C-2 and $R^2$ is a single bond, and the bond between C-2 and C-3 together with the dotted line represents a double bond are preferred in their (2"E)-configuration. As illustrated in the examples the compounds in their (2"E)-configuration possess a more intense odour than the compounds in the corresponding (2"Z)-configuration.

Thus, the present invention refers in a further aspect to compound of formula I wherein the bond between C-2 and $R^2$ is a single bond, and C-2 and C-3 together with the dotted line represents a double bond, enriched in one of the double bond isomers, i.e. (E)- or (Z)-configured double bond.

The term "enriched" is used herein for a compound having an isomeric purity of over 1:1 in favour of the selected double bond isomer. Compounds are preferred having a purity of about 55:45 or greater, e.g. about 70:30.

The compounds according to the present invention may be used alone or in combination with known odourant molecules selected from the extensive range of natural and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example carrier materials, and other auxiliary agents commonly used in the art.

The following list comprises examples of known odourant molecules, which may be combined with the compounds of the present invention:

ethereal oils and extracts, e.g. castoreum, costus root oil, oak moss absolute, geranium oil, jasmine absolute, patchouli oil, rose oil, sandalwood oil or ylang-ylang oil;

alcohols, e.g. citronellol, Ebanol™, eugenol, geraniol, Super Muguet™, linalool, phenylethyl alcohol, Sandalore™, terpineol or Timberol™.

aldehydes and ketones, e.g. α-amylcinnamaldehyde, Georgywood™, hydroxycitronellal, Iso E Super®, Isoraldeine™, Hedione®, maltol, methyl cedryl ketone, methylionone or vanillin;

ether and acetals, e.g. Ambrox™, geranyl methyl ether, rose oxide or Spirambrene™.

esters and lactones, e.g. benzyl acetate, cedryl actetate, γ-decalactone, Helvetolide®, γ-undecalactone or vetivenyl acetate.

macrocycles, e.g. ambrettolide, ethylene brassylate or Exaltolide®.

heterocycles, e.g. isobutylchinoline.

However, due to their unique character, the compounds of formula I are especially well suited for use in fresh musky accords, woody-spicy or floral-hesperidic compositions as is more specifically illustrated in the Example.

The compounds of the present invention may be used in a broad range of fragrance applications, e.g. in any field of fine and functional perfumery, such as perfumes, household products, laundry products, body care products and cosmetics. The compounds can be employed in wide ranging amounts depending upon the specific application and on the nature and quantity of other odourant ingredients that may be, for example, from about 0.001 to about 20 weight percent. In one embodiment compounds of the present invention may be employed in a fabric softener in an amount of about 0.001 to 0.05 weight percent. In another embodiment compounds of the present invention may be used in an alcoholic solution in amounts of about 0.1 to 20 weight percent, more preferably between about 0.1 and 5 weight percent. However, these values should not be limiting on the present invention, since the experienced perfumer may also achieve effects or may create novel accords with lower or higher concentrations.

The compounds of the present invention may be employed into the fragrance application simply by direct mixing the fragrance composition with the fragrance application, or they may, in an earlier step be entrapped with an entrapment material, for example, polymers, capsules, microcapsules and nanocapsules, liposomes, precursors, film formers, absorbents such as for example by using carbon or zeolites, cyclic oligosaccharides and mixtures thereof, or they may be chemically bound to substrates which are adapted to release the fragrance molecule upon application of an exogenous stimulus such as light, enzyme, or the like, and then mixed with the application.

Thus, the invention additionally provides a method of manufacturing a fragrance application, comprising the incorporation of a compound of formula I as a fragrance ingredient, either by directly admixing the compound of formula I to the application or by admixing a fragrance composition comprising a compound of formula I, which may then be mixed to a fragrance application, using conventional techniques and methods.

As used herein, "fragrance application" means any product, such as fine perfumery, e.g. perfume and Eau de Toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odourant. This list of products is given by way of illustration and is not to be regarded as being in any way limiting.

Compounds of formula I wherein X is a divalent radical —(CMe$_2$)-, and Y is oxygen, i.e. oxa esters, may be synthesized by etherification of an appropriately substituted allylic alcohol with isobutylene oxide and subsequent esterification with an appropriately substituted carboxylic acid. The resulting compounds may be hydrogenated in a known manner to give further compounds of formula I.

Compounds of formula I wherein X is carbonyl and Y oxygen, i.e. diesters, may be synthesized by esterification of an appropriately substituted allylic alcohol with chloroacetic acid, followed by further esterification with an appropriately substituted carboxylic acid. The resulting compounds may be hydrogenated in a known manner to give further compounds of formula I.

Compounds of formula I wherein X is carbonyl and Y is a divalent radical —(CH$_2$)—, i.e. oxo esters, may be prepared by esterification of an appropriately substituted allylic alcohol with an appropriately substituted oxo carboxylic acid, e.g. laevulinic acid.

Compounds of formula I wherein X is a divalent radical —(CMe$_2$)- and Y is a divalent radical —(CH$_2$)—, i.e. oxa ketones, may be prepared by etherification of an appropriately substituted allylic alcohol with isobutylene oxide, subsequent oxidation to the aldehyde, followed by Wittig-Horner-Emmons reaction under conditions known to the skilled person and selective hydrogenation of the formed double bond. The resulting compounds may be further hydrogenated in a known manner to give further compounds of formula I.

The aforementioned substituted allylic alcohol starting material is accessible by reduction of an aldol-condensation product, as known in the art.

Further particulars as to reaction conditions are provided in the examples.

There now follows a series of examples that illustrate the invention.

EXAMPLE 1

(2"E/Z) Acetic acid 2'-methyl-2'-(1",2",4"-trimethyl-pent-2"-enyloxy)propyl ester Within a period of 90 min., a solution of triethyl 2-phosphonopropionate (238 g, 1.00 mol) in dimethoxyethane (DME, 150 ml) was added dropwise with stirring under an atmosphere of N$_2$ to a solution of NaH (43.6 g, 1.00 mol) in DME (600 ml). The mixture was then heated to reflux, and after 15 min. at reflux temp., isobutyric aldehyde (72.1 g, 1.00 mol) was added dropwise. After a further 30 min. stirring at reflux, the mixture was poured into ice/water (1:1, 1 L). AcOH (60 ml) was added, and the product was extracted with $Et_2O$ (2×200 ml). The combined organic extracts were washed with water (400 ml) and brine (100 ml), dried ($Na_2SO_4$), and concentrated in a rotary evaporator. The resulting residue was distilled to provide at 86-75° C./27 mbar 117 g (75%) of 2,4-dimethylpent-2-enoic acid ethyl ester.

A mixture of 2,4-dimethylpent-2-enoic acid ethyl ester (116 g, 742 mmol) and KOH 85% (147 g, 2.23 mol) in water/EtOH (1:1, 2.0 L) was refluxed for 1 d. The EtOH was stripped off on a rotary evaporator, and the remaining mixture was washed with $Et_2O$. The combined ethereal washings were extracted with 2 N aq. NaOH (100 ml), and all aqueous solutions were combined. Under cooling with an ice/water bath, conc. aq. $H_3PO_4$ (200 ml) was added to adjust the combined aqueous solutions to pH 3, and the product was extracted with $Et_2O$ (200 ml). The ethereal solution was washed with water (200 ml) and brine (25 ml). After drying ($Na_2SO_4$), the solvent was evaporated in a rotary evaporator to furnish 94.2 g (99%) of 2,4-dimethylpent-2-enoic acid.

Under an atmosphere of $N_2$, a 1.6 M solution of MeLi in $Et_2O$ (500 ml, 800 mmol) was added during 105 min. dropwise with stirring between 0-10° C. to a solution of 2,4-dimethylpent-2-enoic acid (41.0 g, 320 mmol) in $Et_2O$ (1.6 L). The reaction mixture was heated to reflux for 1 h, and then between 5-15° C. 5 N HCl (200 ml) was added dropwise. The organic layer was separated, the aqueous one extracted with $Et_2O$ (200 ml). The combined organic solutions were washed with water (200 ml) and brine (100 ml), dried ($Na_2SO_4$) and concentrated in a rotary evaporator to afford crude 3,5-dimethylhex-3-en-2-one, which was taken up in $Et_2O$ (160 ml). Under $N_2$ at room temp., this solution was added dropwise with stirring to a suspension of LAH (3.34 g, 880 mmol) in $Et_2O$ (320 ml) during 1 h. The reaction mixture was refluxed for 2 h, and then quenched between 0-5° C. by addition of water (10 ml) and brine (20 ml). The organic layer was separated and the aqueous one extracted with $Et_2O$ (100 ml). The combined ethereal extracts were washed with water (100 ml) and brine (50 ml), dried ($Na_2SO_4$), and concentrated under reduced pressure. Silica-gel FC (pentane/$Et_2O$, 4:1, $R_f$=0.40) of the resulting residue provided 34.7 g (85% over 2 steps) of 3,5-dimethylhex-3-en-2-ol.

At 0° C. under $N_2$, a 1 M solution of $MeAlCl_2$ (50 ml, 50 mmol) in hexane was added dropwise with stirring during a period of 1 h to a solution of 3,5-dimethylhex-3-en-2-ol (12.8 g, 100 mmol) and isobutylene oxide (8.65 g, 120 mmol) in cyclohexane (100 ml). The cooling bath was removed, and stirring was continued for 16 h, prior to pouring the mixture into ice/water (1:1, 100 ml). The resulting slurry was dissolved by addition of conc. aq. $H_3PO_4$, and the product extracted with $Et_2O$ (2×100 ml). The combined organic extracts were washed with water (100 ml) and brine (25 ml), dried ($Na_2SO_4$) and concentrated in a rotary evaporator. The resulting residue was purified by silica-gel FC (pentane/$Et_2O$, 19:1, $R_f$=0.12) to afford 3.10 g (15%) of 2-methyl-2-(1',2',4'-trimethylpent-2'-enyloxy)propan-1-ol.

At 0° C. under $N_2$, N,N'-Dicyclohexylcarbodiimide (DCC, 1.03 g, 5.00 mmol) was added to a stirred solution of 2-methyl-2-(1',2',4'-trimethylpent-2'-enyloxy)propan-1-ol (830 mg, 4.14 mmol), acetic acid (250 mg, 4.14 mmol) and 4-(dimethylamino)pyridine (DMAP, 50 mg, 410 mmol) in $CH_2Cl_2$ (10 ml). After stirring for 1 h at room temp., the precipitate was vacuum filtrated and washed with $CH_2Cl_2$. The combined filtrates were concentrated under reduced pressure, and the resulting residue was purified by silica-gel FC (pentane/$Et_2O$, 19:1, $R_f$=0.36) to furnish 710 mg (71%) of the odouriferous title compound.

IR (ATR): ν=1232/1044 $cm^{-1}$ (s, νC—O), 1744 $cm^{-1}$ (s, νO—C=O).—$^1$H NMR ($CDCl_3$): δ=0.91/0.92/0.93/0.95 (4d, J=6.5 Hz, 6H, 4"-$Me_2$), 1.14/1.15 (2d, J=6.5 Hz, 3H, 1"-Me), 1.17/1.18 (2s, 6H, 2'-$Me_2$), 1.60/1.68 (2d, J=1.5 Hz, 3H, 2"-Me), 2.07/2.08 (2s, 3H, 2-$H_3$), 2.48/2.60 ($2m_c$, 1H, 4"-H), 3.89/3.90/3.99/4.00 (4d, J=11.0, 2H, 1'-$H_2$), 4.01/4.57 (2q, J=6.5 Hz, 1H, 1"-H), 4.85/5.14 (2d, J=9.5 Hz, 1H, 3"-H).—$^{13}$C NMR ($CDCl_3$): δ=11.1/17.6 (2q, 2"-Me), 20.7/20.8 (2q, C-2), 22.3/22.4/22.6/22.8/23.1/23.3 (6q, 1"-Me, 4"-$Me_2$), 23.4/23.5/23.5/23.6 (4q, 2'-$Me_2$), 26.4/26.5 (2d, C-4"), 66.0/73.3 (2d, C-1"), 69.7/69.8 (2t, C-1'), 74.1/74.2 (2s, C-2'), 131.6/131.9 (2d, C-3"), 136.3/136.7 (2s, C-2"), 170.7/170.7 (2s, C-1).—MS (70 eV); m/z=242 (1) [$M^+$], 227 (1) [$M^+$-$CH_3$], 199 (1) [$M^+$-$C_3H_7$], 115 (42) [$C_6H_{11}O_2^+$], 111 (46) [$C_8H_{15}^+$], 110 (30) [$C_8H_{14}^+$], 95 (26) [$C_8H_{14}^+$—$CH_3$], 81 (7) [$C_8H_{14}^+$—$C_2H_5$], 69 (45) [$C_8H_{14}^+$—$C_3H_5$], 55 (30) [$C_4H_7^+$], 43 (100) [$C_3H_7^+$].—$C_{14}H_{26}O_3$ (242.4): calcd. C, 69.38; H, 10.81. found C, 69.51; H, 11.02.

Odour description: floral, musky, fruity-green.

GC Olfactometry: (E/Z)=45:55, both isomers smell musky, the E-isomer is more intense.

EXAMPLE 2

(2"E/Z) Propionic acid 2'-methyl-2'-(1",2",4"-trimethylpent-2"-enyloxy)-propyl ester Following the procedure for the synthesis of (2"E/Z) acetic acid 2'-methyl-2'-(1",2",4"-trimethylpent-2"-enyloxy) propyl ester (see Example 1), Steglich esterification of 2-methyl-2-(1',2',4'-trimethylpent-2'-enyloxy)propan-1-ol (830 mg, 4.14 mmol) with propanoic acid (310 mg, 4.14 mmol) and purification by silica-gel FC (pentane/$Et_2O$, 19:1, $R_f$=0.50) furnished 690 mg (65%) of the odouriferous title compound.

IR (ATR): ν=1072/1169 $cm^{-1}$ (s, νC—O), 1741 $cm^{-1}$ (s, νO—C=O).—$^1$H NMR ($CDCl_3$): δ=0.91/0.92/0.93/0.95 (4d, J=6.5 Hz, 6H, 4"-$Me_2$), 1.14/1.15 (2d, J=6.5 Hz, 3H, 1"-Me), 1.16/1.16 (2t, J=8.0 Hz, 3H, 3-$H_3$), 1.17/1.18 (2s, 6H, 2'-$Me_2$), 1.60/1.68 (2d, J=1.5 Hz, 3H, 2"-Me), 2.36/2.36 (2q, J=8.0 Hz, 2H, 2-$H_2$), 2.48/2.59 ($2m_c$, 1H, 4"-H), 3.90/3.91/3.99/4.00 (4d, J=11.0, 2H, 1'-$H_2$), 4.02/4.57 (2q, J=6.5 Hz, 1H, 1"-H), 4.85/5.14 (2d, J=9.5 Hz, 1H, 3"-H).—$^{13}$C NMR ($CDCl_3$): δ=8.96/8.96 (2q, C-3), 11.1/17.6 (2q, 2"-Me), 22.3/22.4/22.6/22.8/23.1/23.3 (6q, 1"-Me, 4"-$Me_2$), 23.4/23.5/23.6/23.6 (4q, 2'-$Me_2$), 26.4/26.5 (2d, C-4"), 27.4/27.5 (2t, C-2), 66.0/73.3 (2d, C-1"), 69.6/69.7 (2t, C-1'), 74.2/74.3 (2s, C-2'), 131.5/131.8 (2d, C-3"), 136.3/136.7 (2s, C-2"), 174.1/174.1 (2s, C-1).—MS (70 eV); m/z=256 (1) [$M^+$], 241 (1) [$M^+$-$CH_3$], 147 (1) [$C_7H_{15}O_3^+$], 129 (27) [$C_7H_{13}O_2^+$], 111 (52) [$C_8H_{15}^+$], 110 (28) [$C_8H_{14}^+$], 95 (26) [$C_8H_{14}^+$—$CH_3$], 81 (9) [$C_8H_{14}^+$—$C_2H_5$], 69 (40) [$C_8H_{14}^+$—$C_3H_5$], 57 (100) [$C_4H_9^+$].—$C_{15}H_{28}O_3$ (256.4): calcd. C, 70.27; H, 11.01. found C, 70.50; H, 11.18.

Odour description: powerful, musky, fruity, slightly green.

GC Olfactometry: (E/Z)=45:55, both isomers smell musky, the E-isomer is more intense.

EXAMPLE 3

(2"E/Z) Cyclopropanecarboxylic acid 2'-methyl-2'-(1",2",4"-trimethyl-pent-2"-enyl-oxy)propyl ester Following the procedure for the synthesis of (2"E/Z) acetic acid 2'-methyl-2'-(1",2",4"-trimethylpent-2"enyloxy) propyl ester (see Example 1), Steglich esterification of 2-methyl-2-(1',2',4'-trimethylpent-2'-enyloxy)propan-1-ol (830 mg, 4.14 mmol) with cyclopropane carboxylic acid (360 mg, 4.14 mmol) and purification by silica-gel FC (pentane/Et$_2$O, 99:1, R$_f$=0.07) furnished 680 mg (61%) of the odouriferous title compound.

IR (ATR): ν=1163/1072 cm$^{-1}$ (s, νC—O), 1731 cm$^{-1}$ (s, νO—C=O).—$^1$H NMR (CDCl$_3$): δ=0.85/0.85 (2 m$_c$, 2H, 3-,4-H$_b$), 0.91/0.92/0.95/0.95 (4d, J=6.5 Hz, 6H, 4"-Me$_2$), 1.00/1.01 (2m$_c$, 2H, 3-,4-H$_a$), 1.14/1.15 (2d, J=6.5 Hz, 3H, 1"-Me), 1.17/1.18/1.18/1.19 (4s, 6H, 2'-Me$_2$), 1.63/1.64 (2m$_c$, 2H, 2-H), 1.60/1.69 (2d, J=1.5 Hz, 3H, 2"-Me), 2.49/2.61 (2m$_c$, 1H, 4"-H), 3.89/3.90/3.99/4.01 (4d, J=11.0, 2H, 1'-H$_2$), 4.01/4.58 (2q, J=6.5 Hz, 1H, 1"-H), 4.85/5.14 (2d, J=9.5 Hz, 1H, 3"-H).—$^{13}$C NMR (CDCl$_3$): δ=8.13/8.13/8.15/8.15 (4q, C-3,-4), 11.1/17.6 (2q, 2"-Me), 12.7/12.8 (2d, C-2), 22.3/22.4/22.7/22.8/23.1/23.3 (6q, 1"-Me, 4"-Me$_2$), 23.5/23.6/23.6/23.6 (4q, 2'-Me$_2$), 26.4/26.5 (2d, C-4"), 66.0/73.3 (2d, C-1"), 69.6/69.7 (2t, C-1'), 74.2/74.3 (2s, C-2'), 131.6/131.9 (2d, C-3"), 136.3/136.7 (2s, C-2"), 174.4/174.5 (2s, C-1).—MS (70 eV); m/z=268 (1) [M$^+$], 253 (1) [M$^+$-CH$_3$], 225 (1) [M$^+$-C$_3$H$_7$], 159 (2) [C$_8$H$_{15}$O$_3^+$], 141 (17) [C$_8$H$_{13}$O$_2^+$], 111 (38) [C$_8$H$_{15}^+$], 110 (20) [C$_8$H$_{14}^+$], 95 (16) [C$_8$H$_{14}^+$—CH$_3$], 81 (6) [C$_8$H$_{14}^+$—C$_2$H$_5$], 69 (100) [C$_8$H$_{14}^+$—C$_3$H$_5$], 55 (21) [C$_4$H$_7^+$], 41 (27) [C$_3$H$_5^+$].—C$_{16}$H$_{28}$O$_3$ (268.4): calcd. C, 71.60; H, 10.52. found C, 71.66; H, 10.70.

Odour description: powerful, musky, sweet, slightly fruity.

GC Olfactometry: (E/Z)=45:55, both isomers smell musky, the E-isomer is more intense.

EXAMPLE 4 a: (2"E/Z) Butyric acid 2'-methyl-2'-(1",2",4"-trimethylpent-2"-enyloxy)propyl ester Following the procedure for the synthesis of (2"-E/Z) acetic acid 2'-methyl-2'-(1",2",4"-trimethylpent-2"-enyloxy) propyl ester (see Example 1), Steglich esterification of 2-methyl-2-(1',2',4'-trimethylpent-2'-enyloxy)propan-1-ol (1.72 g, 8.59 mmol) with butyric acid (2.43 ml, 26.4 mmol) and purification by silica-gel FC (pentane/Et$_2$O, 19:1, R$_f$=0.42) furnished 2.30 g (99%) of the odouriferous title compound.

IR (ATR): ν=1168/1073 cm$^{-1}$ (s, νC—O), 1739 cm$^{-1}$ (s, νO—C=O).—$^1$H NMR (CDCl$_3$): δ=0.90/0.92/0.93/0.94 (4d, J=6.5 Hz, 6H, 4"-Me$_2$), 0.95/0.96 (2t, J=7.5 Hz, 3H, 4-H$_3$), 1.14/1.15 (2d, J=6.5 Hz, 3H, 1"-Me), 1.17/1.18 (2s, 6H, 2'-Me$_2$), 1.60/1.68 (2d, J=1.5 Hz, 3H, 2"-Me), 1.62-1.70 (m, 2H, 3-H$_2$), 2.32 (br. t, J=7.5 Hz, 2H, 2-H$_2$), 2.49/2.60 (2m$_c$, 1H, 4"-H), 3.90/3.91/3.99/4.00 (4d, J=11.0, 2H, 1'-H$_2$), 4.02/4.58 (2q, J=6.5 Hz, 1H, 1"-H), 4.85/5.14 (2d, J=9.5 Hz, 1H, 3"-H).—$^{13}$C NMR (CDCl$_3$): δ=11.2/17.8 (2q, 2"-Me), 13.7/13.7 (2q, C-4), 18.3/18.4 (2t, C-3), 22.4/22.5/22.7/22.8/22.9/23.3 (6q, 1"-Me, 4"-Me$_2$), 23.4/23.5/23.7/23.8 (4q, 2'-Me$_2$), 26.5/26.6 (2d, C-4"), 36.1/36.2 (2t, C-2), 66.1/73.5 (2d, C-1"), 69.6/69.8 (2t, C-1'), 74.3/74.4 (2s, C-2'), 131.7/132.0 (2d, C-3"), 136.5/136.8 (2s, C-2"), 173.4/173.5 (2s, C-1).—MS (70 eV) m/z=270 (1) [M$^+$], 255 (1) [M$^+$-CH$_3$], 143 (30) [C$_8$H$_{15}$O$_2^+$], 127 (8) [C$_8$H$_{15}$O$^+$], 111 (79) [C$_8$H$_{15}^+$], 95 (25) [C$_8$H$_{14}^+$—CH$_3$], 81 (10) [C$_8$H$_{14}^+$—C$_2$H$_5$], 71 (100) [C$_4$H$_7$O$^+$], 69 (48) [C$_8$H$_{14}^+$—C$_3$H$_5$], 43 (48) [C$_3$H$_7^+$].

Odour description: musky, fruity, animalic.

b: Butyric acid 2'-methyl-2'-(1",2",4"-trimethylpentyloxy)propyl ester

A suspension of butyric acid 2'-methyl-2'-(1",2",4"-trimethylpent-2"-enyloxy)propyl ester (1.00 g, 3.70 mmol) and 10% Pd/C (100 mg, 0.09 mmol) in EtOAc (12 ml), was trice evacuated and flushed with N$_2$. Following two cycles of flushing and evacuating with H$_2$, the reaction mixture was stirred at room temp. for 3 h under a positive pressure of H$_2$. The catalyst was removed by vacuum filtration over a pad of Celite, and the filtrate was concentrated under reduced pressure. Silica-gel FC (pentane/Et$_2$O, 19:1, R$_f$=0.40) of the resulting residue furnished 980 mg (98%) of the odouriferous title compound.

IR (ATR): ν=1168/1105/1072 cm$^{-1}$ (s, νC—O), 1739 cm$^{-1}$ (s, νO—C=O).—$^1$H NMR (CDCl$_3$): δ=0.82/0.84 (2d, J=7.0 Hz, 3H, 2"-Me), 0.85/0.90 (2d, J=7.0 Hz, 6H, 4"-Me$_2$), 0.93-1.16 (m, 2H, 3"-H$_2$), 0.95/0.96 (2t, J=7.5 Hz, 3H, 4-H$_3$), 0.99/1.03 (2d, J=6.5 Hz, 3H, 1"-Me), 1.18 (br. s, 6H, 2'-Me$_2$), 1.62 (m$_c$, 2H, 2"-,4"-H), 1.68 (m$_c$, 2H, 3-H$_2$), 2.32/2.33 (2t, J=7.5 Hz, 2H, 2-H$_2$), 3.54 (m$_c$, 1H, 1"-H), 3.94 (br. s, 2H, 1'-H$_2$).—$^{13}$C NMR (CDCl$_3$): δ=13.7/13.9 (2q, C-4), 15.9/17.4 (2q, 2"-Me), 17.4/18.7 (2q, 1"-Me), 18.4/18.4 (2t, C-3), 21.6/22.0/23.7/23.7 (4q, 4"-Me$_2$), 23.8/23.8/23.9/24.0 (4q, 2'-Me$_2$), 25.2/25.3 (2d, C-4"), 36.2/36.3 (2t, C-2), 36.8/37.1 (2d, C-2"), 40.9/43.0 (2t, C-3"), 70.1/70.3 (2t, C-1'), 70.8/71.4 (2d, C-1"), 73.6/73.7 (2s, C-2'), 173.4/173.5 (2s, C-1).—MS (70 eV); m/z=187 (1) [M$^+$-C$_6$H$_{13}$], 171 (2) [M$^+$-C$_5$H$_9$O], 143 (75) [C$_8$H$_{15}$O$_2^+$], 113 (27) [C$_8$H$_{17}^+$], 71 (100) [C$_4$H$_7$O$^+$], 57 (30) [C$_4$H$_9^+$], 43 (44) [C$_3$H$_7^+$].—C$_{16}$H$_{32}$O$_3$ (272.43): calcd. C, 70.54; H, 11.84. found C, 70.41; H, 11.73.

Odour description: musky, sweet, fruity, floral.

EXAMPLE 5

(2"E/Z) Isobutyric acid 2'-methyl-2'-(1",2",4"-trimethylpent-2"-enyloxy)propyl ester Following the procedure for the synthesis of (2"E/Z) acetic acid 2'-methyl-2'-(1",2",4"-trimethylpent-2"-enyloxy) propyl ester (see Example 1), Steglich esterification of 2-methyl-2-(1',2',4'-trimethylpent-2'-enyloxy)propan-1-ol (1.72 g, 8.59 mmol) with isobutyric acid (2.45 ml, 26.4 mmol) and purification by silica-gel FC (pentane/Et$_2$O, 19:1, R$_f$=0.50) furnished 1.94 g (84%) of the odouriferous title compound.

IR (ATR): ν=1072/1153 cm$^{-1}$ (s, νC—O), 1737 cm$^{-1}$ (s, νO—C=O).—$^1$H NMR (CDCl$_3$): δ=0.91/0.92/0.93/0.95 (4d, J=6.5 Hz, 6H, 4"-Me$_2$), 1.14/1.15 (2d, J=6.5 Hz, 3H, 1"-Me), 1.17/1.18 (2s, 6H, 2'-Me$_2$), 1.19/1.20 (2d, J=6.5 Hz, 6H, 2-Me$_2$), 1.60/1.68 (2d, J=1.5 Hz, 3H, 2"-Me), 2.45-2.67 (m, 1H, 2-H), 2.48/2.58 (2m$_c$, 1H, 4"-H), 3.89/3.90/3.99/4.00 (4d, J=11.0, 2H, 1'-H$_2$), 4.00/4.59 (2q, J=6.5 Hz, 1H, 1"-H), 4.85/5.14 (2d, J=9.5 Hz, 1H, 3"-H).—$^{13}$C NMR (CDCl$_3$): δ=11.2/17.8 (2q, 2"-Me), 18.90/18.91/18.94/18.95 (4q, 2-Me$_2$), 22.4/22.5/22.7/22.8/22.9/23.2 (6q, 1"-Me, 4"-Me$_2$), 23.4/23.5/23.7/23.8 (4q, 2'-Me$_2$), 26.5/26.6 (2d, C-4"), 34.0/34.0 (2d, C-2), 66.1/73.5 (2d, C-1"), 69.6/69.7 (2t, C-1'), 74.4/74.5 (2s, C-2'), 131.7/132.0 (2d, C-3"), 136.5/136.8 (2s, C-2"), 176.7/176.8 (2s, C-1).—MS (70 eV); m/z=270 (1) [M$^+$], 255 (1) [M$^+$-CH$_3$], 227 (1) [M$^+$-C$_3$H$_7$], 143 (33) [C$_8$H$_{15}$O$_2^+$], 127 (10) [C$_8$H$_{15}$O$^+$], 111 (93) [C$_8$H$_{15}^+$], 95 (29) [C$_8$H$_{14}^+$—CH$_3$], 81 (13) [C$_8$H$_{14}^+$—C$_2$H$_5$], 71 (100) [C$_4$H$_7$O$^+$], 69 (57) [C$_8$H$_{14}^+$—C$_3$H$_5$], 43 (80) [C$_3$H$_7^+$].

Odour description: musky, fruity, rosy.

EXAMPLE 6

(2"E/Z) 2-Methylacrylic acid 2'-methyl-2'-(1",2",4"-trimethylpent-2"-enyloxy)propyl ester Following the procedure for the synthesis of (2"E/Z) acetic acid 2'-methyl-2'-(1",2",4"-trimethylpent-2"-enyloxy) propyl ester (see Example 1), Steglich esterification of 2-methyl-2-(1',2',4'-trimethylpent-2'-enyloxy)propan-1-ol (1.72 g, 8.59 mmol) with 2-methylacrylic acid (2.45 ml, 26.4 mmol) and purification by silica-gel FC (pentane/Et$_2$O, 19:1, R$_f$=0.37) furnished 1.93 g (84%) of the odouriferous title compound.

IR (ATR): ν=1156/1073 cm$^{-1}$ (s, νC—O), 1721 cm$^{-1}$ (s, νO—C=O).—$^1$H NMR (CDCl$_3$): δ=0.91/0.92/0.93/0.95 (4d, J=6.5 Hz, 6H, 4"-Me$_2$), 1.14/1.15 (2d, J=6.5 Hz, 3H, 1"-Me), 1.20/1.21 (2s, 6H, 2'-Me$_2$), 1.60/1.68 (2d, J=1.5 Hz, 3H, 2"-Me), 1.97 (m$_c$, 3H, 2-Me), 2.45/2.61 (2m$^c$, 1H, 4"-H), 3.97/3.98/3.99/4.03 (4d, J=11.0, 2H, 1'-H$_2$), 4.07/4.60 (2q, J=6.5 Hz, 1H, 1"-H), 4.85/5.14 (2d, J=9.5 Hz, 1H, 3"-H), 5.57/6.14 (m$_c$, 2H, 3-H$_2$).—$^{13}$C NMR (CDCl$_3$): δ=11.2/17.7 (2q, 2"-Me), 18.3/22.4/22.5/22.5/22.7/22.8/22.9/23.3 (8q, 2-Me, 1"-Me, 4"-Me$_2$), 23.5/23.7/23.8/23.8 (4q, 2'-Me$_2$), 26.5/26.6 (2d, C-4"), 66.1/73.5 (2d, C-1"), 70.0/70.1 (2t, C-1'), 74.4/74.5 (2s, C-2'), 125.3/125.4 (2t, C-3), 131.7/132.0 (2d, C-3"), 136.3/136.4/136.5/136.8 (4s, C-2,-2"), 167.1/167.2 (2s, C-1).—MS (70 eV); m/z=159 (1) [C$_8$H$_{15}$O$_3^+$], 141 (22) [C$_8$H$_{13}$O$_2^+$], 127 (6) [C$_8$H$_{15}$O$^+$], 111 (44) [C$_8$H$_{15}$], 95 (18) [C$_8$H$_{14}^+$—CH$_3$], 85 (5) [C$_4$H$_5$O$_2^+$], 81 (7) [C$_8$H$_{14}^+$—C$_2$H$_5$], 69 (100) [C$_4$H$_5$O$^+$], 55 (22) [C$_4$H$_7^+$], 41 (35) [C$_3$H$_5^+$].

Odour description: intense musky, slightly floral, fruity, rosy.

EXAMPLE 7

(2E, 2"E/Z) But-2-enoic acid 2'-methyl-2'-(1",2",4"-trimethylpent-2"-enyloxy)propyl ester Following the procedure for the synthesis of (2"E/Z) acetic acid 2'-methyl-2'-(1",2",4"-trimethylpent-2"-enyloxy) propyl ester (see Example 1), Steglich esterification of 2-methyl-2-(1',2',4'-trimethylpent-2'-enyloxy)propan-1-ol (1.72 g, 8.59 mmol) with trans-crotonic acid (2.27 g, 26.4 mmol) and purification by silica-gel FC (pentane/Et$_2$O, 19:1, R$_f$=0.38) furnished 2.05 g (89%) of the odouriferous title compound.

IR (ATR): ν=1169/1074 cm$^{-1}$ (s, νC—O), 1722 cm$^{-1}$ (s, νO—C=O), 1660 cm$^{-1}$ (s, νC=C).—$^1$H NMR (CDCl$_3$): δ=0.90/0.92/0.93/0.95 (4d, J=6.5 Hz, 6H, 4"-Me$_2$), 1.14/1.15 (2d, J=6.5 Hz, 3H, 1"-Me), 1.19/1.20 (2s, 6H, 2'-Me$_2$), 1.59/1.67 (2d, J=1.5 Hz, 3H, 2"-Me), 1.89/1.88 (2d, J=7.0 Hz, 3H, 4-H$_3$), 2.46/2.60 (2m$_c$, 1H, 4"-H), 3.95/3.96/4.02/4.04 (4d, J=11.0 Hz, 2H, 1'-H$_2$), 4.05/4.59 (2q, J=6.5 Hz, 1H, 1"-H), 4.84/5.14 (2d, J=9.5 Hz, 1H, 3"-H), 5.88 (br. dq, J=15.5, 1.5 Hz, 1H, 2-H), 6.97/7.01 (2dq, J=15.5, 7.0 Hz, 1H, 3-H).—$^{13}$C NMR (CDCl$_3$): δ=11.2/17.8 (2q, 2"-Me), 17.9/17.9 (2q, C-4), 22.4/22.5/22.5/22.7/22.9/23.3 (6q, 1"-Me, 4"-Me$_2$), 23.5/23.6/23.7/23.8 (4q, 2'-Me$_2$), 26.5/26.6 (2d, C-4"), 66.1/73.5 (2d, C-1"), 69.5/69.6 (2t, C-1'), 74.5/74.5 (2s, C-2'), 122.5/122.7 (2d, C-2), 131.7/132.0 (2d, C-3"), 136.5/136.8 (2s, C-2"), 144.5/144.6 (2d, C-3), 166.3/166.3 (2s, C-1).—MS (70 eV); m/z=253 (1) [M$^+$-CH$_3$], 159 (1) [C$_8$H$_{15}$O$_3^+$], 141 (16) [C$_8$H$_{13}$O$_2^+$], 127 (6) [C$_8$H$_{15}$O$^+$], 111 (35) [C$_8$H$_{15}^+$], 95 (14) [C$_8$H$_{14}^+$—CH$_3$], 81 (7) [C$_8$H$_{14}^+$—C$_2$H$_5$], 69 (100) [C$_4$H$_5$O$^+$], 55 (18) [C$_4$H$_7^+$], 41 (21) [C$_3$H$_5^+$].

Odour description: intense musky, fruity-floral undertones, sweet.

EXAMPLE 8

(2"E/Z) But-3-enoic acid 2'-methyl-2'-(1",2",4"-trimethylpent-2"-enyloxy)propyl ester Following the procedure for the synthesis of (2"E/Z) acetic acid 2'-methyl-2'-(1",2",4"-trimethylpent-2"-enyloxy) propyl ester (see Example 1), Steglich esterification of 2-methyl-2-(1',2',4'-trimethylpent-2'-enyloxy)propan-1-ol (1.72 g, 8.59 mmol) with but-3-enoic acid (2.27 g, 26.4 mmol) and purification by silica-gel FC (pentane/Et$_2$O, 19:1, R$_f$=0.33) furnished 2.21 g (96%) of the odouriferous title compound.

IR (ATR): ν=1164/1073 cm$^{-1}$ (s, νC—O), 1741 cm$^-$(s, νO—C=O), 1644 cm$^{-1}$ (s, νC=C).—$^1$H NMR (CDCl$_3$): δ=0.91/0.92/0.93/0.95 (4d, J=6.5 Hz, 6H, 4"-Me$_2$), 1.13/1.14 (2d, J=6.5 Hz, 3H, 1"-Me), 1.17/1.18 (2s, 6H, 2'-Me$_2$), 1.60/1.68 (2d, J=1.5 Hz, 3H, 2"-Me), 2.47/2.59 (2m$_c$, 1H, 4"-H), 3.12 (br. dt, J=7.0, 1.5 Hz, 2H, 2-H$_2$), 3.92/3.93/4.01/4.02 (4d, J=11.0 Hz, 2H, 1'-H$_2$), 3.97/4.57 (2q, J=6.5 Hz, 1H, 1"-H), 4.85/5.14 (2d, J=9.5 Hz, 1H, 3"-H), 5.15-5.20 (m, 2H, 4-H$_2$), 5.96 (m$_c$, 1H, 3-H).—$^{13}$C NMR (CDCl$_3$): δ=11.2/17.8 (2q, 2"-Me), 22.4/22.5/22.5/22.7/22.8/23.3 (6q, 1"-Me, 4"-Me$_2$), 23.5/23.6/23.7/23.7 (4q, 2'-Me$_2$), 26.5/26.6 (2d, C-4"), 39.1/39.2 (2t, C-2), 66.2/73.5 (2d, C-1"), 70.1/70.2 (2t, C-1'), 74.3/74.4 (2s, C-2'), 118.5/118.6 (2t, C-4), 125.3/125.4 (2t, C-4), 130.2/132.0 (2d, C-3"), 131.7/131.7 (2d, C-3), 136.5/136.8 (2s, C-2"), 171.3/171.3 (2s, C-1).—MS (70 eV); m/z=268 (1) [M$^+$], 253 (1) [M$^+$-CH$_3$], 141 (28) [C$_8$H$_{13}$O$_2^+$], 127 (5) [C$_8$H$_{15}$O$^+$], 111 (56) [C$_8$H$_{15}^+$], 95 (26) [C$_8$H$_{14}^+$—CH$_3$], 85 (8) [C$_4$H$_5$O$_2^+$], 81 (9) [C$_8$H$_{14}^+$—C$_2$H$_5$], 69 (100) [C$_4$H$_5$O$^+$], 55 (29) [C$_4$H$_7^+$], 41 (51) [C$_3$H$_5^+$].

Odour description: strong musky with fruit-green nuances, floral.

EXAMPLE 9

(2"E/Z) Propionic acid (1",2",4"-trimethyl pent-2"-enyloxy)carbonylmethyl ester A solution of N,N'-dicyclohexylcarbodiimide (DCC, 5.99 g, 29.0 mmol) in CH$_2$Cl$_2$ (13 ml) was added dropwise to a stirred solution of 3,5-dimethylhex-3-en-2-o (4.00 g, 9.36 mmol) and 4-(dimethylamino)pyridine (DMAP, 320 mg, 2.64 mmol) in CH$_2$Cl$_2$ (26 ml). The reaction mixture was stirred for 5 min. at room temp., prior to vacuum filtration of the yellow precipitate. The precipitate was washed with CH$_2$Cl$_2$ (2×), and the combined filtrates were concentrated under reduced pressure. The crude material (7.70 g) was purified by silica-gel FC (pentane/Et$_2$O, 19:1, R$_f$=0.54) to provide 1.15 g (60%) of chloroacetic acid 1',2',4'-trimethylpent-2'-enyl ester.

A mixture of chloroacetic acid 1',2',4'-trimethylpent-2'-enyl ester (1.09 g, 5.33 mmol), propionic acid (0.39 g, 5.33 mmol) and K$_2$CO$_3$ (1.47 g, 10.6 mmol) in Et$_2$CO/dioxane (4:1, 12.5 ml) was refluxed for 2 days, with another portion of K$_2$CO$_3$ (1.47 g, 10.6 mmol) being added after 1 day. The reaction mixture was then poured into ice/water (1:1, 50 ml), and the product was extracted with Et$_2$O (2×50 ml). The combined ethereal extracts were washed with water (50 ml) and brine (25 ml), dried (Na$_2$SO$_4$) and concentrated under reduced pressure. Silca-gel FC (pentane/Et$_2$O, 19:1, R$_f$=0.23) of the resulting residue afforded 0.71 g (55%) of the odouriferous the compound.

IR (ATR): ν=1162/1059 cm$^{-1}$ (s, νC—O), 1748 cm$^{-1}$ (s, νO—C=O).—$^1$H NMR (CDCl$_3$): δ=0.91/0.93/0.94/0.96 (4d, J=6.5 Hz, 6H, 4"-Me$_2$), 1.19 (t, J=7.5 Hz, 3H, 3-H, 3-H$_3$), 1.31/1.32 (2d, J=6.5 Hz, 3H, 1"-Me), 1.62/1.66 (2d, J=1.5 Hz, 3H, 2"-Me), 2.45/2.46 (2q, J=8.0 Hz, 2H, 2-H$_2$), 2.65/2.68 (2m$_c$, 1H, 4"-H), 4.53/4.57 (2d, J=17.0 Hz, 1H, 2'-H$_b$), 4.59/4.61 (2d, J=17.0 Hz, 1H, 2'-H$_a$), 5.07/5.27 (2 br. d, J=10.0 Hz, 1H, 3"-H), 5.31/5.84 (2q, J=6.5 Hz, 1H, 1"-H).—$^{13}$C NMR (CDCl$_3$): δ=8.89/8.89 (2q, C-3), 17.5/18.0 (2q, 2"-Me), 23.0/23.3/26.6/26.7/27.0/27.1 (6q, 1"-,4"-Me$_2$), 26.6/26.7 (2d, C-4"), 27.0/27.2 (2t, C-2), 60.6/60.7 (t, C-2'), 70.4/76.9 (2d, C-1"), 130.6/131.2 (2s, C-2"), 135.5/136.6 (2d, C-3"), 167.0/167.1 (s, C-1'), 173.6/173.6 (s, C-1).—MS (70 eV); m/z=242 (1) [M$^+$], 128 (4) [C$_8$H$_{16}$O$^+$], 115 (80) [C$_5$H$_7$O+], 110 (54) [C$_8$H$_{14}$$^+$], 95 (86) [C$_8$H$_{14}$$^+$—CH$_3$], 87 (39) [C$_4$H$_7$O$_2$$^+$], 81 (16) [C$_8$H$_{14}$$^+$—C$_2$H$_5$], 67 (39) [C$_8$H$_{14}$$^+$—C$_3$H$_7$], 57 (100) [C$_4$H$_9$$^+$].

Odour description: musky, sweet, green, fruity.

EXAMPLE 10

(2'E/Z)-6-Methyl-6-(1',2',4'-trimethylpent-2'-enyloxy)heptan-3-one

A solution of pyridinium chlorochromate (PCC, 43.3 g, 201 mmol) in CH$_2$Cl$_2$ (350 ml) was added in one dash to a stirred slurry of Celite® (50 g) in CH$_2$Cl$_2$ (900 ml). Stirring was continued for 15 min., prior to dropwise addition of 2-methyl-2-(1',2',4'-trimethylpent-2'-enyloxy)propan-1-ol (see Example 1, 11.8 g, 58.9 mmol) in CH$_2$Cl$_2$ (350 ml) in the course of 20 min. The reaction mixture was stirred at room temp. for 1 d, with a further portion of PCC (4.30 g, 20.0 mmol) being added after the first 5 h, and then filtered by suction over a pad of Celite®. The filtrate was concentrated in a rotary evaporator, and the resulting residue purified by silica-gel FC (pentane/Et$_2$O, 19:1, R$_f$=0.57) to furnish 9.97 g (85%) of 2-methyl-2-(1',2',4'-trimethylpent-2'-enyloxy)propionaldehyde.

A solution of diethyl (2-oxobutyl)phosophonate (5.25 g, 25.2 mmol) in DME (5 ml) was added dropwise to a stirred suspension of 95% NaH (640 mg, 25.2 mmol) in DME (15 ml). The reaction mixture was refluxed for 15 min. prior to the dropwise addition of 2-methyl-2-(1',2',4'-trimethylpent-2'-enyloxy)propionaldehyde (5.00 g, 25.2 mmol). After further 2 h at reflux, the reaction mixture was poured into ice/water (1:1, 100 ml), acidified with AcOH, and extracted with Et$_2$O (2×50 ml). The combined ethereal extracts were washed with water (50 ml) and brine (25 ml), dried (Na$_2$SO$_4$) and concentrated under reduced pressure. Silica-gel FC (pentane/Et$_2$O, 19:1, R$_f$=0.22) of the resulting residue provided 2.11 g (33%) of 6-methyl-6-(1',2',4'-trimethylpent-2'-enyloxy)hept-4-en-3-one, possessing a relatively weak green, floral and cinnamic odor without pronounced musk character.

Under an atmosphere of N$_2$, [(PPh$_3$)CuH]$_6$ (5.83 g, 2.97 mmol) was dissolved in deoxygenated benzene. After stirring for 5 min., 6-methyl-6-(1',2',4'-trimethylpent-2'-enyloxy)hept-4-en-3-one (2.05 g, 8.12 mmol) was added dropwise during 5 min., and the reaction mixture was stirred 5 h at room temp. under an atmosphere of N$_2$. Then the inert gas supply was removed, and the dark red suspension was stirred under humid air for 30 min., during which the color of the reaction mixture turned dark brown. The insoluble material was removed by vacuum filtration over a pad of Celite® and washed with toluene, and the combined organic solutions were evaporated in a rotary evaporator. The resulting residue was purified by silica-gel FC (pentane/Et$_2$O, 19:1, R$_f$=0.14) to furnish 1.68 g (81%) of the odouriferous title compound.

IR (ATR): ν=1112 cm$^{-1}$ (s, νC—O), 1716 cm$^{-1}$ (s, νC=O).—$^1$H NMR (CDCl$_3$): δ=0.90/0.91/0.91/0.93 (4d, J=7.0 Hz, 6H, 4'-Me$_2$), 1.05/1.06 (2t, J=7.0 Hz, 3H, 1-H$_3$), 1.11/1.12 (2d, J=6.5 Hz, 3H, 1'-Me), 1.11/1.14 (2s, 6H, 6-Me$_2$), 1.16-1.77 (m, 2H, 5-H$_2$), 1.58/1.67 (2d, J=1.5 Hz, 3H, 2'-Me), 2.41-2.63 (m, 5H, 2-,4-H$_2$, 4'-H), 3.92/4.49 (2q, J=6.5 Hz, 1H, 1'-H), 4.83/5.10 (2 br. d, J=9.5 Hz, 1H, 3'-H).—$^{13}$C NMR (CDCl$_3$): δ=7.85/7.87 (2q, C-1), 11.3/17.9 (2q, 2'-Me), 22.5/22.6/22.8/22.9/23.5/26.0 (6q, 1'-,4'-Me$_2$), 26.5/26.6 (2d, C-4'), 34.9/35.0/35.8/35.9/37.2/37.3 (6t, C-2,-4,-5), 65.4/74.7 (2d, C-1'), 72.9/74.6 (2s, C-6), 131.6/131.9 (2s, C-2'), 136.7/136.9 (2d, C-3'), 211.8 (s, C-3).—MS (70 eV); m/z=254 (1) [M$^+$], 211 (1) [M$^+$-C$_3$H$_7$], 145 (2) [C$_8$H$_{17}$O$_2$$^+$], 127 (89) [C$_8$H$_{15}$O$^+$], 111 (42) [C$_8$H$_{15}$$^+$], 110 (32) [C$_8$H$_{14}$$^+$], 95 (36) [C$_8$H$_{14}$$^+$—CH$_3$], 85 (7) [C$_8$H$_{15}$O$^+$—C$_3$H$_6$], 69 (44) [C$_8$H$_{14}$$^+$—C$_3$H$_5$], 57 (100) [C$_4$H$_9$$^+$].

Odour description: powerful, pleasant musky note, sweet, fruity.

EXAMPLE 11

6-Methyl-6-(1',2',4'-trimethylpentyloxy)heptan-3-one

Following the procedure for the preparation of butyric acid 2'-methyl-2'-(1",2",4"-trimethylpentyloxy)propyl ester (see Example 4) (2'E/Z)-6-methyl-6-(1',2',4'-trimethylpent-2'-enyloxy)heptan-3-one (1.07 g, 4.21 mmol) was hydrogenated in the presence of 10% Pd/C (100 mg, 0.09 mmol) to provide after purification by bulb-to-bulb distillation (125° C., 0.9 mbar) 750 mg (70%) of the odouriferous title compound.

IR (ATR): ν=1108 cm$^{-1}$ (s, νC—O), 1716 cm$^{-1}$ (s, νC=O).—$^1$H NMR (CDCl$_3$): δ=0.80/0.83 (2 br. d, J=7.0 Hz, 6H, 4'-Me$_2$), 0.89/0.90/0.95/0.99 (4d, J=6.5 Hz, 6H, 1'-,2'-Me), 1.06/1.06 (2t, J=7.5 Hz, 3H, 1-H$_3$), 1.10/1.11/1.14/1.14 (4s, 6H, 6-Me$_2$), 1.22-1.79 (m, 6H, 5-,3'-H$_2$, 2'-,4'-H), 2.42-2.54 (m, 4H, 2-,4-H$_2$), 3.44/3.47 (2q, J=6.5, 4.5 Hz, 1H, 1'-H).—$^{13}$C NMR (CDCl$_3$): δ=7.88/7.88 (2q, C-1), 13.9/16.0/17.1/18.4 (4q, 1'-,2'-Me), 21.7/22.1/23.6/24.1/25.6125.7/26.2/26.4 (8q, 6-,4'-Me$_2$), 25.2/25.3 (2d, C-4'), 35.8/35.8/35.9/36.1/37.2/37.3 (6t, C-2,-4,-5), 36.8/37.1 (2d, C-2'), 40.7/43.2 (2t, C-3'), 70.0/70.6 (2d, C-1'), 73.8/73.9 (2s, C-6), 211.8/211.9 (2s, C-3).—MS (70 eV); m/z=241 (1) [M$^+$-CH$_3$], 171 (2) [C$_{11}$H$_{23}$O$^+$], 127 (100) [C$_8$H$_{15}$O$^+$], 113 (7) [C$_8$H$_{17}$$^+$], 109 (14) [C$_8$H$_{15}$O$^+$—H$_2$O], 97 (6) [C$_7$H$_{13}$$^+$], 71 (11) [C$_5$H$_{11}$$^+$], 57 (85) [C$_4$H$_9$$^+$].

Odor description: musky, sweet, slightly fruity-floral.

EXAMPLE 12

(2"E)-Propionic acid 2'-methyl-2'-(1",4",4"-trimethylpent-2"-enyloxy)-propyl ester Following the procedure of C. Börner, M. R. Dennis, E. Sinn, S. Woodward, *Eur. J. Org. Chem*. 2001, 2435-2446, (3E)-5,5-dimethylhex-3-en-2-one was prepared. Standard LAH reduction (vide supra) furnished (3E)-5,5-dimethylhex-3-en-2-ol after purification by silica-gel FC (pentane/Et$_2$O, 4:1, R$_f$=0.31). Following the general procedure of Example 1 (3E)-5,5-dimethylhex-3-en-2-ol (29.4 g, 229 mmol) was etherified with isobutylene oxide (19.8 g, 275 mmol) to provide after silica-gel FC (pentane/Et$_2$O, 9:1, R$_f$=0.27) 4.21 g (8%) of 2-methyl-2-(1',4',4'-trimethylpent-2'-enyloxy)propan-1-ol. According to the synthesis of (2"E/Z)-acetic acid 2'-methyl-2'-(1",2",4"-trimethylpent-2"-enyloxy)propyl ester (vide supra), Steglich esterification of 2-methyl-2-(1',4',4'-trimethylpent-2'-enyloxy)propan-1-ol (1.30 g, 6.49 mmol) with propionic acid (480 mg, 6.49 mmol) and silica-gel FC (pentane/Et$_2$O, 19:1, R$_f$=0.14) furnished 1.37 g (82%) of the odouriferous title compound.

IR (ATR): ν=1169/1063 cm$^{-1}$ (s, νC—O), 1741 cm$^{-1}$ (s, νO—C=O).—$^1$H NMR (CDCl$_3$): δ=0.99 (s, 9H, 4"-Me$_3$), 1.16 (t, J=7.0 Hz, 3H, 3-H$_3$), 1.17 (d, J=6.5 Hz, 3H, 1"-Me), 1.19 (s, 6H, 2'-Me$_2$), 2.37 (q, J=7.0 Hz, 2H, 2-H$_2$), 3.94 (d, J=11.0 Hz, 1H, 1'-H$_b$), 4.00 (d, J=11.0 Hz, 1H, 1'-H$_a$), 4.14 (quint. d, J=6.5, 1.0 Hz, 1H, 1"-H), 5.34 (dd, J=15.5, 6.5 Hz, 1H, 2"-H), 5.54 (dd, J=15.5, 1.0 Hz, 1H, 3"-H).—$^{13}$C NMR (CDCl$_3$): δ=9.09 (q, C-3), 23.8/23.9/23.9 (3q, 2'-,1"-Me), 27.6 (t, C-2), 29.4 (3q, 4"-Me$_3$), 32.5 (s, C-4"), 69.1 (d, C-1"), 69.8 (t, C-1'), 74.4 (s, C-2'), 129.3 (d, C-2"), 140.3 (d, C-3"), 174.2 (s, C-1).—MS (70 eV); m/z=241 (1) [M$^+$-CH$_3$], 129 (20) [C$_8$H$_{17}$O$^+$], 127 (9) [C$_8$H$_{15}$O$^+$], 111 (100) [C$_8$H$_{15}$$^+$], 95 (16) [C$_7$H$_{11}$$^+$], 69 (43) [C$_8$H$_{14}$$^+$—C$_3$H$_5$], 57 (92) [C$_4$H$_9$$^+$].

Odour description: musky, sweet, green, grapefruit.

EXAMPLE 13

(2"E)-Cyclopropanecarboxylic acid 2'-methyl-2'-(1", 4",4"-trimethylpent-2"-enyloxy)propyl ester According to the synthesis of (2"E/Z)acetic acid 2'-methyl-2'-(1",2",4"-trimethylpent-2"-enyloxy)propyl ester (see Example 1), Steglich esterification of 2-methyl-2-(1',4',4'-trimethylpent-2'-enyloxy)propan-1-ol (1.30 g, 6.49 mmol) with cyclopropanecarboxylic acid (590 mg, 6.49 mmol) and silica-gel FC (pentane/Et$_2$O, 19:1, R$_f$=0.29) furnished 1.46 g (84%) of the odouriferous title compound.

IR (ATR): ν=1163/1063 cm$^{-1}$ (s, νC—O), 1731 cm$^{-1}$ (s, νO—C=O).—$^1$H NMR (CDCl$_3$): δ=0.86 (m$_c$, 2H, 3-,4-H$_b$), 0.99 (s, 9H, 4"-Me$_3$), 1.02 (m$_c$, 2H, 3-,4-H$_a$), 1.17 (d, J=6.5 Hz, 3H, 1"-Me), 1.20 (s, 6H, 2'-Me$_2$), 1.66 (m$_c$, 1H, 2-H), 3.93 (d, J=11.5 Hz, 1H, 1'-H$_b$), 3.99 (d, J=11.5 Hz, 1H, 1'-H$_a$), 4.13 (quint. d, J=6.5, 1.0 Hz, 1H, 1"-H), 5.35 (dd, J=15.5, 6.5 Hz, 1H, 2"-H), 5.54 (dd, J=15.5, 1.0 Hz, 1H, 3"-H).—$^{13}$C NMR (CDCl$_3$): δ=8.33 (2t, C-3,-4), 12.9 (d, C-2), 23.9/23.9/24.0 (3q, 2'-,1"-Me), 29.4 (3q, 4"-Me$_3$), 32.5 (s, C-4"), 69.1 (d, C-1"), 69.8 (t, C-1'), 74.4 (s, C-2'), 129.3 (d, C-2"), 140.3 (d, C-3"), 174.6 (s, C-1).—MS (70 eV); m/z=253 (1) [M$^+$-CH$_3$], 141 (13) [C$_8$H$_{13}$O$_2$$^+$], 127 (9) [C$_8$H$_{15}$O$^+$], 111 (78) [C$_8$H$_{15}$$^+$], 95 (14) [C$_7$H$_{11}$$^+$], 69 (100) [C$_8$H$_{14}$$^+$—C$_3$H$_5$], 41 (33) [C$_3$H$_5$$^+$].

Odour description: musky, sweet, fruity, powdery, anisic.

EXAMPLE 14

(2"E)-Butyric acid 2'-methyl-2'-(1",4",4"-trimethylpent-2"-enyloxy)-propyl ester According to the synthesis of (2"E/Z)-acetic acid 2'-methyl-2'-(1",2",4"-trimethylpent-2"-enyloxy)propyl ester (see Example 1), Steglich esterification of 2-methyl-2-(1',4',4'-trimethylpent-2'-enyloxy)propan-1-ol (1.30 g, 6.49 mmol) with butyric acid (570 mg, 6.49 mmol) and silica-gel FC (pentane/Et$_2$O, 19:1, R$_f$=0.26) furnished 1.45 g (83%) of the odouriferous title compound.

IR (ATR): ν=1168/1062 cm$^{-1}$ (s, νC—O), 1738 cm$^{-1}$ (s, νO—C=O).—$^1$H NMR (CDCl$_3$): δ=0.96 (t, J=7.5 Hz, 3H, 4-H$_3$), 0.99 (s, 9H, 4"-Me$_3$), 1.16 (d, J=6.5 Hz, 3H, 1"-Me), 1.20 (s, 6H, 2'-Me$_2$), 1.68 (sext., J=7.5 Hz, 2H, 3-H$_2$), 2.33 (t, J=7.5 Hz, 2H, 2-H$_2$), 3.94 (d, J=11.5 Hz, 1H, 1'-H$_b$), 4.02 (d, J=11.0 Hz, 1H, 1'-H$_a$), 4.13 (quint. d, J=6.5, 1.0 Hz, 1H, 1"-H), 5.35 (dd, J=15.5, 6.5 Hz, 1H, 2"-H), 5.54 (dd, J=15.5, 1.0 Hz, 1H, 3"-H).—$^{13}$C NMR (CDCl$_3$): δ=13.7 (q, C-4), 18.4 (t, C-3), 23.8/23.9/24.0 (3q, 2'-,1"-Me), 29.4 (3q, 4"-Me$_3$), 32.5 (s, C-4"), 36.2 (t, C-2), 69.1 (d, C-1"), 69.7 (t, C-1'), 74.4 (s, C-2'), 129.3 (d, C-2"), 140.3 (d, C-3"), 173.4 (s, C-1).—MS (70 eV); m/z=143 (15) [C$_8$H$_{15}$O$_2$$^+$], 127 (10) [C$_8$H$_{15}$O$^+$], 111 (100) [C$_8$H$_{15}$$^+$], 95 (16) [C$_7$H$_{11}$$^+$], 71 (66) [C$_4$H$_7$O$^+$], 69 (39) [C$_8$H$_{14}$$^+$—C$_3$H$_5$], 55 (29) [C$_4$H$_7$$^+$], 43 (41) [C$_3$H$_7$$^+$].

Odour description: fruity, musky.

EXAMPLE 15

(2'E)-4-Oxopentanoic acid 1',4',4'-trimethylpent-2'-enyl ester

Steglich esterification of (3E)-5,5-dimethylhex-3-en-2-ol (760 mg, 5.93 mmol), following the general synthesis protocol described above, with 4-oxopentanoic acid (690 mg, 5.93 mmol) gave after the usual work-up and purification by silica-gel FC (pentane/Et$_2$O, 9:1, R$_f$=0.14) 1.21 g (90%) of the odouriferous title compound.

IR (ATR): ν=1721 cm$^{-1}$ (s, νC=O), 1159 cm$^{-1}$ (s, νC—O),.—$^1$H NMR (CDCl$_3$): δ=1.00 (s, 9H, 4'-Me$_3$), 1.28 (d, J=6.0 Hz, 3H, 1'-Me), 2.19 (s, 3H, 5-H$_3$), 2.56 (t, J=7.0, 2H, 2-H$_2$), 2.74 (td, J=7.0, 2.5, 2H, 3-H$_2$), 5.28-5.38 (m, 2H, 1'-,2'-H), 5.69 (d, J=14.5 Hz, 1H, 3'-H).—$^{13}$C NMR (CDCl$_3$): δ=20.4 (q, 1'-Me), 28.4 (t, C-2), 29.3 (3q, 4'-Me$_3$), 29.8 (q, C-5), 32.7 (s, C-4'), 37.9 (t, C-3), 71.6 (d, C-1'), 124.2 (d, C-2'), 143.9 (d, C-3'), 171.9 (s, C-1), 206.6 (s, C-4).—MS (70 eV); m/z=208 (1) [M$^+$-H$_2$O], 170 (5) [M$^+$-C$_4$H$_8$$^+$], 152 (1) [M$^+$-C$_4$H$_8$—H$_2$O], 127 (11) [C$_8$H$_{15}$O$^+$], 110 (16) [C$_8$H$_{15}$$^+$], 99 (100) [C$_5$H$_7$O$_2$$^+$], 95 (55) [C$_8$H$_{15}$$^+$—CH$_3$], 81 (9) [C$_5$H$_7$O$_2$$^+$—H$_2$O], 67 (25) [C$_5$H$_7$$^+$], 55 (30) [C$_4$H$_7$$^+$], 43 (37) [C$_2$H$_3$O$^+$].

Odour description: fresh, musky, slightly metallic, pear, ambrette seed oil.

EXAMPLE 16

(2"E)-Propionic acid 2'-(1",4"-dimethylpent-2"-enyloxy)-2'-methylpropyl ester

Following the preparation of (2"E)-propionic acid 2'-methyl-2'-(1",4",4"-trimethylpent-2"-enyloxy)propyl ester (see Example 12), standard LAH reduction of commercially available (3E)$_5$-methylhex-3-en-2-one (150 g, 1.34 mol) afforded at 74-80° C./160 mbar 109 g (88%) of (3E)-5-methylhex-3-en-2-ol, of which 108 g (946 mmol) was etherified with isobutylene oxide (81.8 g, 1.14 mmol) to provide after silica-gel FC (pentane/Et$_2$O, 9:1, R$_f$=0.17) 24.8 g (14%) of 2-methyl-2-(1',4'-dimethylpent-2'-enyloxy)propan-1-ol. Steglich esterification of 2-methyl-2-(1',4'-dimethylpent-2'-enyloxy)propan-1-ol (1.80 g, 9.66 mmol) with propionic acid (1.19 g, 16.1 mmol) and usual work-up with silica-gel FC (pentane/Et$_2$O, 19:1, R$_f$=0.31) furnished 1.00 g (43%) of the odouriferous title compound.

IR (ATR): ν=1168/1057 cm⁻¹ (s, νC—O), 1741 cm⁻¹ (s, νO—C=O).—¹H NMR (CDCl₃): δ=0.96/0.97 (2d, J=7.0 Hz, 6H, 4"-Me₂), 1.16 (t, J=7.5 Hz, 3H, 3-H₃), 1.17 (d, J=6.5 Hz, 3H, 1"-Me), 1.20 (s, 6H, 2'-Me₂), 2.24 (br. oct., J=7.0 Hz, 1H, 4"-H), 2.37 (q, J=7.5 Hz, 2H, 2-H₂), 3.95 (d, J=11.5 Hz, 1H, 1'-H_b), 3.99 (d, J=11.5 Hz, 1H, 1'-H_a), 4.12 (br. quint., J=6.5 Hz, 1H, 1"-H), 5.38 (ddd, J=15.5, 6.5, 1.0 Hz, 1H, 2"-H), 5.50 (ddd, J=15.5, 6.5, 1.0 Hz, 1H, 3"-H).—¹³C NMR (CDCl₃): δ=9.09 (q, C-3), 21.2/22.2 (2q, 4"-Me), 23.7/23.8/23.9 (3q, 2'-,1"-Me), 27.6 (t, C-2), 30.5 (d, C-4"), 68.8 (d, C-1"), 69.7 (t, C-1'), 74.4 (s, C-2'), 131.5 (d, C-2"), 136.4 (d, C-3"), 174.2 (s, C-1).—MS (70 eV); m/z=227 (1) [M⁺-CH₃], 146 (1) [C₇H₁₄O₃⁺], 129 (15) [C₈H₁₇O⁺], 113 (8) [C₇H₁₃O⁺], 97 (100) [C₇H₁₃⁺], 57 (80) [C₄H₉⁺], 55 (56) [C₇H₁₃⁺—C₃H₆].

Odour description: musky, fruity, earthy, green.

EXAMPLE 17

(2"E)-Cyclopropanecarboxylic acid 2'-(1",4"-dimethylpent-2"-enyloxy)-2'-methylpropyl ester Steglich esterification of 2-methyl-2-(1',4'-dimethylpent-2'-enyloxy)propan-1-ol (1.80 g, 9.66 mmol) with cyclopropanecarboxylic acid (1.40 g, 16.1 mmol) and usual work-up with silica-gel FC (pentane/Et₂O, 19:1, R_f=0.28) provided 900 mg (37%) of the odouriferous title compound.

IR (ATR): ν=1162 cm⁻¹ (s, νC—O), 1730 cm⁻¹ (s, νO—C=O).—¹H NMR (CDCl₃): δ=0.86 (m_c, 2H, 3-,4-H_b), 0.96/0.97 (2d, J=7.0 Hz, 6H, 4"-Me₂), 1.02 (m_c, 2H, 3-,4-H_a), 1.17 (d, J=6.5 Hz, 3H, 1"-Me), 1.21 (s, 6H, 2'-Me₂), 1.65 (m_c, 1H, 2-H), 2.24 (br. oct., J=7.0 Hz, 1H, 4"-H), 3.94 (d, J=11.0 Hz, 1H, 1'-H_b), 3.98 (d, J=11.0 Hz, 1H, 1'-H_a), 4.12 (br. quint., J=6.5 Hz, 1H, 1"-H), 5.39 (ddd, J=15.5, 6.5, 1.0 Hz, 1H, 2"-H), 5.51 (ddd, J=15.5, 6.5, 1.0 Hz, 1H, 3"-H).—¹³C NMR (CDCl₃): δ=8.29/8.30 (2t, C-3,-4), 12.9 (d, C-2), 22.1/22.2 (2q, 4"-Me₂), 23.7/23.8/23.9 (3q, 2'-,1"-Me), 30.5 (d, C-4"), 68.8 (d, C-1"), 69.7 (t, C-1'), 74.4 (s, C-2'), 131.5 (d, C-2"), 136.4 (d, C-3"), 174.6 (s, C-1).—MS (70 eV); m/z=239 (1) [M⁺-CH₃], 158 (1) [C₈H₁₄O₃⁺], 141 (13) [C₈H₁₃O₂⁺], 127 (1) [C₈H₁₅O⁺], 110 (12) [C₈H₁₄⁺], 97 (100) [C₇H₁₃⁺], 69 (100) [C₄H₅O⁺], 55 (57) [C₇H₁₃⁺—C₃H₆], 41 (36) [C₃H₅⁺].

Odor description: musky, fruity, floral.

EXAMPLE 18

Masculine Fine Fragrance

| compound/ingredient | parts by weight 1/1000 |
|---|---|
| 1. 2-Acetyl-1,2,3,4,5,6,7,8-octahydro-1,2,8,8-tetramethylnaphthalene (Georgywood ™) | 40.00 |
| 2. Benzyl salicylate | 150.00 |
| 3. Bergamot oil, Italy | 10.00 |
| 4. Butyl hydroxy toluene | 2.00 |
| 5. Cardamom oil, Guatemala | 1.00 |
| 6. Cyclohexadec-5-ene-1-one (Velvione ™) | 10.00 |
| 7. alpha-Cyclohexylidenebenzeneacetonitrile (Peonile ™) | 60.00 |
| 8. Diethylphthalate | 285.00 |
| 9. Dihydro myrcenol | 25.00 |
| 10. 4-(1-Ethoxyethenyl)-3,3,5,5-tetramethylcyclohexanone (Kephalis ™) | 50.00 |

-continued

| compound/ingredient | parts by weight 1/1000 |
|---|---|
| 11. Ethyl 2-ethyl-6,6-dimethyl-2-cyclohexencarboxylate (Givescone ™) | 2.00 |
| 12. 6-Ethyl-3-methyloct-6-en-1-ol (Super Muguet ™) | 13.00 |
| 13. Grapefruit oil | 5.00 |
| 14. Lavender oil, France | 5.00 |
| 15. Linalool, synthetic | 30.00 |
| 16. [1-Methyl-2-(1,2,2-trimethylbicyclo[3.1.0]hex-3-ylmethyl)cyclopropyl[methanol (Javanol ™) | 1.00 |
| 17. Pepper oil | 10.00 |
| 18. Rose absolute | 1.00 |
| 19. (2"EIZ) Cyclopropanecarboxylic acid 2'-methyl-2'-(1",2",4"-trimethylpent-2"-enyloxy) propyl ester | 300.00 |
| | 1000.00 |

The (2"E/Z)-cyclopropanecarboxylic acid 2'-methyl-2'-(1",2",4"-trimethylpent-2"-enyloxy)propyl ester conveys to this fragrance a very pleasant, sensual musk tonality. It adds volume, sweetness and warmth to the composition. In addition it provides fixative properties to the fragrance; yet, the musk characteristics are present from the top note impressions till the dry down of this perfume.

The invention claimed is:
1. A compound of formula I

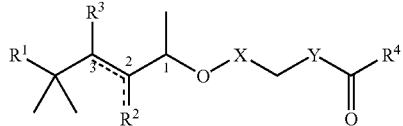

wherein
R¹ and R³ are independently hydrogen, methyl, or ethyl;
R² is hydrogen, methyl, ethyl, methylene, or ethylidene;
R⁴ is C₁ to C₄ alkyl; or
R⁴ is vinyl or a linear, branched or cyclic C₃ to C₄ alkenyl;
X is carbonyl or a divalent radical —(CMe₂)-;
Y is oxygen or a divalent radical —(CH₂)—;
the bond between C-2 and R² is a single bond, and the bond between C-2 and C-3 together with the dotted line represents a double bond; or
the bond between C-2 and C-3 is a single bond, and the bond between C-2 and R² together with the dotted line represents a double bond; or
the bond between C-2 and R² is a single bond and the bond between C-2 and C-3 is a single bond.

2. A compound according to claim 1 wherein the bond between C-2 and R² is a single bond, and the bond between C-2 and C-3 together with the dotted line represents a double bond.

3. A compound according to claim 1 selected from the group consisting of acetic acid 2'-methyl-2'-(1",2",4"-trimethylpent-2"-enyloxy)propyl ester, propionic acid 2'-methyl-2'-(1",2",4"-trimethylpent-2"-enyloxy)propyl ester, cyclopropanecarboxylic acid 2'-methyl-2'-(1",2",4"-trimethylpent-2"-enyloxy)propyl ester, butyric acid 2'-methyl-2'-(1",2",4"-trimethylpent-2"-enyloxy)propyl ester, isobutyric acid 2'-methyl-2'-(1",2",4"-trimethylpent-2"-enyloxy)propyl ester, 2-methylacrylic acid 2'-methyl-2'-(1",2",4"-trimethylpent-2"-enyloxy)propyl ester, but-2- enoic acid 2'-methyl-2'-(1",2",4"-trimethylpent-2"-enyloxy) propyl ester, but-3-enoic acid 2'-methyl-2'-(1",2",4"-trigmethylpent-2"-enyloxy)propyl ester, propionic acid (1",2",4"-trimethylpent-2"-enyloxy)carbonylmethyl ester, 6-methyl-6-(1', 2',4'-trimethylpent-2'-enyloxy)heptan-3-one, propionic acid 2'-methyl-2'-(1",4",4"-trimethylpent-2"-enyloxy)propyl ester, cyclopropanecarboxylic acid 2'-methyl-2'-(1",4",4"-trimethylpent-2"-enyloxy)propyl ester, butyric acid 2'-methyl-2'-(1",4",4"-trimethylpent-2"-enyloxy)propyl ester, 4-oxopentanoic acid 1',4',4'-trimethylpent-2'-enyl ester, propionic acid 2'-(1",4"-dimethylpent-2"-enyloxy)-2'-methylpropyl ester, cyclopropanecarboxylic acid 2'-(1",4"-dimethylpent-2"-enyloxy)-2'-methyipropyl ester, butyric acid 2'-methyl-2'-(1",2",4"-trimethylpentyloxy)propyl ester, and 6-methyl-6-(1',2',4'-trimethylpentyloxy)heptan-3-one.

4. A compound according to claim 2 characterised in that it is enriched in the (2"E)-isomer.

5. A compound according to claim 2 characterised in that it is enriched in the (2"Z)-isomer.

6. A fragrance composition comprising a compound according to claim 1.

7. A fragrance application comprising a compound as defined in claim 1, or a mixture thereof.

8. A fragrance application according to claim 7 wherein the fragrance application is a perfume, household product, laundry product, body care product or cosmetic product.

9. A method of manufacturing a fragrance application, comprising the step of incorporating a compound of formula I as defined in claim 1 to a perfume, household product, laundry product, body care product or cosmetic product.

10. A fragrance application comprising a compound as defined in claim 3, or a mixture thereof.

* * * * *